United States Patent [19]
Hafner

[11] Patent Number: 6,103,504
[45] Date of Patent: Aug. 15, 2000

[54] PROCESS FOR PRODUCTION OF AVERMECTINS AND CULTURES THEREFOR

[75] Inventor: Edmund W. Hafner, East Lyme, Conn.

[73] Assignee: Pfizer Inc., New York, N.Y.

[21] Appl. No.: 07/857,540

[22] Filed: Mar. 25, 1992

[51] Int. Cl.⁷ ............... C12N 1/20; C12P 19/62; C12P 17/18
[52] U.S. Cl. .......... 435/119; 435/172.1; 435/253.5; 435/886
[58] Field of Search .................. 435/253.5, 119, 435/886, 172.1

[56] References Cited

U.S. PATENT DOCUMENTS

| | | | |
|---|---|---|---|
| 4,134,973 | 1/1979 | Fisher et al. | 424/180 |
| 4,156,720 | 5/1979 | Fisher et al. | 424/180 |
| 4,199,569 | 4/1980 | Chabala et al. | 424/180 |
| 4,200,581 | 4/1980 | Fisher et al. | 424/180 |
| 4,285,963 | 8/1981 | Arison et al. | 424/279 |
| 4,310,519 | 1/1982 | Albers-Schonberg et al. | 424/181 |
| 4,328,335 | 5/1982 | Mrozik | 536/7.1 |
| 4,333,925 | 6/1982 | Buhs et al. | 424/181 |
| 4,378,353 | 3/1983 | Goegelman et al. | 424/181 |
| 4,423,209 | 12/1983 | Mrozik | 536/7.1 |
| 4,429,042 | 1/1984 | Albers-Schonberg et al. | 435/119 |
| 4,831,016 | 5/1989 | Mrozik | 514/30 |
| 5,077,278 | 12/1991 | Hafner et al. | 514/30 |
| 5,089,480 | 2/1992 | Gibson et al. | 514/30 |
| 5,234,831 | 8/1993 | Hafner et al. | 435/253.5 |
| 5,238,848 | 8/1993 | Hafner et al. | 435/253.5 |
| 5,240,850 | 8/1993 | Lam et al. | 435/253.5 |

FOREIGN PATENT DOCUMENTS

| | | |
|---|---|---|
| 1689 | 5/1979 | European Pat. Off. . |
| 2615 | 6/1979 | European Pat. Off. . |
| 7812 | 2/1980 | European Pat. Off. . |
| 214731 | 3/1987 | European Pat. Off. . |
| 215654 | 3/1987 | European Pat. Off. . |
| 235085 | 9/1987 | European Pat. Off. . |
| 241147 | 10/1987 | European Pat. Off. . |
| 276103 | 7/1988 | European Pat. Off. . |
| 284176 | 9/1988 | European Pat. Off. . |
| 317148 | 5/1989 | European Pat. Off. . |
| 445460 | 9/1991 | European Pat. Off. . |
| 2166436 | 5/1986 | United Kingdom . |
| 2167751 | 6/1986 | United Kingdom . |
| 2170499 | 8/1986 | United Kingdom . |
| 2176182 | 12/1986 | United Kingdom . |

OTHER PUBLICATIONS

Fisher and Mrozik, *Macrolide Antibiotics*, Academic Press (1984), Chp. 14.
Willecke, et al. J. Biol. Chem. 246:5264–5272 (1971).
Martin, et al., J. Bacteriology 115:198–204 (1973).
Schulman, et al., J. Antibiot. 38(11):1494–1498 (1985).
Ruby, et al., 6th Int. Symposium on the "Biology of Actinomycetes", Debrecen, Hungary, Aug. 26–30 (1985).
Schulman, et al., Antimicrobial Agents and Chemotherapy 31:744–747 (1987).
Schulman, et al., Fed. Proc. 44:931 (1985).
Schulman, et al., Antimicrobial Agents and Chemotherapy 29:620–624 (1986).
Tabor, et al., J. Bacteriol. 128:485–486 (1976).
Chen, et al., Abstr. Pap. Am. Chem. Soc., 1983, 186 Meet. MBTD 28.
Cheremisinoff, P. N. and Ouellette, R. P., Eds., *Biotechnology*, 1985, Technomic Publishing Co., Inc., pp. 14–15.
Hafner, E. W. et al., J. Antibiotics 44:349–356 (1991).
Dutton, C. J. et al., J. Antibiotics 44:357–365 (1991).

*Primary Examiner*—Herbert J. Lilling
*Attorney, Agent, or Firm*—Peter C. Richardson; Gregg C. Benson

[57] ABSTRACT

This invention relates to *Streptomyces avermitilis* lacking branched-chain amino acid transaminase activity, branched-chain 2-oxo acid biosynthetic activity and, optionally and preferably, avermectin B-O-methyl transferase activity, methods for preparation thereof, and use thereof to produce natural and non-natural avermectins from branched-chain fatty acid or branched-chain 2-oxo acid precursors. Such avermectins are useful as parasiticides.

25 Claims, No Drawings

PROCESS FOR PRODUCTION OF AVERMECTINS AND CULTURES THEREFOR

BACKGROUND OF THE INVENTION

1. Field of the Invention

This invention relates to strains of *Streptomyces avermitilis* lacking branched-chain amino acid transaminase activity (ilvE) and branched-chain 2-oxo acid biosynthetic activity ("early ilv"), and, optionally and preferably, lacking avermectin B-O-methyl transferase activity, to methods for producing said *S. avermitilis* and to the use of *S. avermitilis* to produce natural and non-natural avermectins using branched-chain fatty acid or branched-chain 2-oxo acid compounds, or derivatives or precursors thereof.

2. General Background

U.S. Pat. Nos. 4,310,519 and 4,429,042 describe the avermectins, a complex of related agents having potent antiparasitic activity, and their production by aerobic fermentation of strains of *Streptomyces avermitilis*; namely, *S. avermitilis* ATCC Nos. 31267, 31271 and 31272. The last two strains cited represent a frozen vial and a lyophilized tube, respectively of a culture obtained by ultraviolet irradiation of *S. avermitilis* ATCC 31267.

EP 214,731, published Mar. 18, 1987, the counterpart of U.S. patent application Ser. No. 886,867, filed Jul. 16, 1986, discloses, inter alia, a number of compounds (referred to herein as non-natural avermectins) related to the natural or known avermectins but having novel substituent groups at the 25-position, a process for their preparation by fermentation of an avermectin producing organism in the presence of certain specified carboxylic acids, or derivatives or precursors thereof, and compositions and methods for treating and preventing insect or parasite infections or infestations comprising such non-natural avermectins. The *S. avermitilis* organisms used to produce the said novel C-25 substituted avermectins are *S. avermitilis* ATCC 31267, 31271, 31272 and NCIB 12121. The latter organism, described in EP 214,731, is derived from *S. avermitilis* ATCC 31271. It gives improved yields of the novel C-25 substituted avermectins when it is cultured in a semi-defined medium. Each of ATCC 31267, 31271, 31272 and NCIB 12121 may also produce, in addition to the novel C-25 substituted derivative, varying amounts of the known, or natural, avermectins wherein the 25-substituent is isopropyl or (S)-sec-butyl (1-methylpropyl).

The carbon skeleton of the avermectins (depicted in formula (I) below) is derived from acetate and propionate precursors and the C-25 substituent of natural avermectins from L-isoleucine (R=(S)-sec-butyl) or L-valine (R=isopropyl) (Fisher and Mrozik, "Macrolide Antibiotics", Academic Press (1984) Ch. 14).

By "known" or "natural" avermectins is meant those avermectins produced by *S. avermitilis* ATCC 31267, ATCC 31271 and ATCC 31272 wherein the 25-position substituent is either isopropyl or (S)-sec-butyl(1-methylpropyl). Avermectins wherein the 25-position substituent is other than isopropyl or sec-butyl (S-form) are referred to herein as novel or non-natural avermectins.

The strains of *S. avermitilis* cited in the above-mentioned U.S. patents produce a class of substances described generically therein as C-076. The class comprises eight distinct but closely related compounds described as C-076, A1a, A1b, A2a, A2b, B1a, B1b, B2a and B2b. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively. Lastly, the numeral "1" refers to avermectins wherein a double bond is present at the 22–23 position; and numeral "2" to avermectins having two hydrogens at the 22-position and a hydroxy and a hydrogen at the 23 position.

In this application no such identifiers are used as regards the 25-substituent of the non-natural avermectins. Identifiers A1, A2, B1 and B2 have been retained to refer to non-natural avermectins having the structural features corresponding to those of the natural avermectins as noted above.

Generation of mutants devoid of branched-chain 2-oxo acid dehydrogenase activity has been reported for *Bacillus subtilis*, Willecke and Pardee, J. Biol. Chem. 246, 5264–72 (1971) and *Pseudomonas putida*, Martin et al., J. Bacteriology, 115 198–204 (1973).

*S. avermitilis* Agly-1, a mutant strain which produces virtually only avermectin aglycones A1a and A2a is reported by Schulman et al. J. Antibiot. 38(11), 1494–1498 (1985). Also reported is the fermentation of *S. avermitilis* Agly-1 in the presence of sinefungin which caused increased production of avermectin aglycone B components. Likewise, *S. avermitilis* 08, a high producing strain for avermectins, when fermented in the presence of sinefungin as inhibitor of O-methyl transferases, resulted in production of avermectins lacking O-methyl groups on the aglycone at C-5 and in the oleandrose disaccharide moiety.

U.S. Pat. No. 4,378,353 describes C-076 related compounds and their preparation by cultivation of MA-5218, a mutant strain of *S. avermitilis* ATCC 31272, obtained therefrom by ultraviolet irradiation. The mutant is identified as ATCC 31780. The C-076 related compounds produced by said mutant lack the C-076 furan ring. Additionally, in certain of the compounds reported, one or both of the oleandrose sugar moieties are absent while in others the 5-position group is a keto group.

Three classes of O-methyl transferase mutants of *S. avermitilis* that produce avermectins lacking O-methyl groups have been reported by Ruby et al., 6th International Symposium on the "Biology of Actinomycetes", Debrecen, Hungary, Aug. 26–30 (1985) and by Schulman et al., Antimicrobial Agents and Chemotherapy 31, 744–7 (1987). The first class produces primarily B avermectins due to their inability to methylate the C-5 hydroxyl of the macrocyclic lactone ring (hereinafter referred to as lacking avermectin B-O-methyl transferase activity). The second class produces 3'-O-bis-demethylavermectins (avermectins lacking the O-methyl substituent at the 3 position of both oleandrose monosaccharide residues), and which are referred to as demethylavermectins. The third class is unable to methylate at any position.

Schulman et al., Fed. Proc. 44, 931 (1985) disclosed increased production of B avermectins by fermenting *S. avermitilis* in the presence of substances such as sinefungin, S-adenosylethionine and S-adenosylhomocysteine which inhibit the methylation of the C-5 hydroxy group of the aglycone moiety by the enzyme avermectin B-O-methyl transferase. *Streptomyces avermitilis* mutants which lack O-methyl transferase activity and produce increased amounts of avermectin B components are also disclosed and referred to by Schulman et al. in Antimicrobial Agents and Chemotherapy 29, 620–624 (1986).

EP 284,176, filed in the name of the assignee hereof and published Sep. 28, 1988, the counterpart of U.S. patent application Ser. No. 107,825, filed Oct. 13, 1987, now abandoned in favor of pending U.S. patent application Ser. No. 660,912, filed Feb. 27, 1991, and assigned to the assignee hereof, discloses, inter alia, strains of *Streptomyces avermitilis* lacking branched-chain amino acid transaminase activity and/or branched-chain 2-oxo acid dehydrogenase activity, methods for producing such *S. avermitilis* strains, and use of such strains to produce natural and non-natural avermectins. Included among the *S. avermitilis* strains disclosed therein are those deposited as ATCC 53567, a *S. avermitilis* strain lacking branched-chain 2-oxo acid dehydrogenase activity, and ATCC 53670, a *S. avermitilis* strain lacking branched-chain amino acid transaminase activity and branched-chain 2-oxo acid dehydrogenase activity.

U.S. Pat. No. 5,077,278, assigned to the assignee hereof, discloses, inter alia, non-natural demethylavermectins and a process for producing non-natural demethylavermectins comprising fermentation of *Streptomyces avermitilis* strains lacking branched-chain 2-oxo acid dehydrogenase activity.

EP 276,103, filed in the name of the assignee hereof and published Jul. 27, 1988, the counterpart of U.S. patent application Ser. No. 126,650, filed Dec. 1, 1987, now abandoned in favor of pending U.S. patent application Ser. No. 660,971, filed Feb. 26, 1991, and assigned to the assignee hereof, discloses, inter alia, *Streptomyces avermitilis* strains lacking branched-chain 2-oxo acid dehydrogenase activity and avermectin B-O-methyl transferase activity, methods for producing such *S. avermitilis* strains and use of such *S. avermitilis* strains to produce natural and non-natural B avermectins.

EP 317,148, published May 24, 1989, the counterpart of U.S. patent application Ser. No. 249,749, filed Sep. 27, 1988, now abandoned in favor of pending U.S. patent application Ser. No. 647,674 filed Jan. 25, 1991, discloses, inter alia, non-natural avermectins related to the natural or known avermectins but having novel substituent groups at the 25-position which groups do not contain an α-branched carbon atom bound to the carbon atom at the 25-position and a process for their preparation by fermentation of *S. avermitilis* lacking branched-chain 2-oxo acid dehydrogenase activity, particularly *S. avermitilis* ATCC 53567 and ATCC 53568. Also disclosed therein are compositions and methods for treating and preventing insect or parasite infections or infestations comprising such non-natural avermectins.

Mutants of *S. avermitilis* lacking branched-chain amino acid transaminase activity and branched-chain 2-oxo acid biosynthetic activity and, optionally, lacking avermectin B-O-methyl transferase activity, no longer possess the ability to produce significant amounts of the natural avermectins in the absence of added compound R—COOH wherein R is isopropyl or (S)-sec-butyl, or of a compound convertible to R—COOH during the fermentation process. Surprisingly and unexpectedly, however, the mutants have been found to produce avermectins, natural and non-natural, when fermented in the presence of an added compound R—COOH or

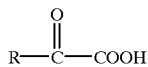

wherein R is isopropyl or (S)-sec-butyl, or other groups disclosed herein, or of a precursor thereof. It is even more surprising that the herein described mutants, which are unable to degrade L-isoleucine, L-leucine or L-valine and which require these three amino acids in order to grow are able to assimilate a wide variety of compounds into the avermectin biosynthetic pathway with production of non-natural avermectins.

The ability to produce avermectins using branched-chain fatty acid or branched-chain 2-oxo acid precursors is a desirable goal.

SUMMARY OF THE INVENTION

*S. avermitilis* strains lacking both branched-chain amino acid transaminase activity (ilvE) and branched-chain 2-oxo acid biosynthetic activity ("early ilv"), and, optionally and preferably, lacking avermectin B-O-methyl transferase activity can be produced by protoplast fusion of *S. avermitilis* mutant strains which lack branched-chain amino acid transaminase activity with *S. avermitilis* mutant strains which lack branched-chain 2-oxo acid biosynthetic activity. Each or one of such strains can optionally lack avermectin B-O-methyl transferase activity. The *S. avermitilis* strains used for such protoplast fusions can be derived by mutation from *S. avermitilis* ATCC 53567 and ATCC 53670. However, at most, only one of such strains used for fusion can lack branched-chain 2-oxo acid dehydrogenase activity as the strains of this invention require the presence of branched-chain 2-oxo acid dehydrogenase activity to utilize branched-chain 2-oxo acids or precursors thereof in the synthesis of avermectins. As used herein, the term mutant also includes the fusant or fusants obtained by such fusion. The resulting mutants are unable to synthesize substantial amounts of natural avermectins except where the fatty acid or a precursor thereof, bearing the isopropyl or sec-butyl (S-form) group is added to the medium in which the mutants are fermented. They are capable of producing substantial amounts of natural and non-natural avermectins when fermented under aqueous aerobic conditions in a nutrient medium containing an appropriate primer acid or compound convertible thereto in the fermentation process.

Those mutants used herein for genetic recombination and which are characterized by their lack of branched-chain amino acid transaminase activity are selected from mutagenized colonies on the basis of their inability to grow on a defined minimal medium which lacks L-isoleucine, L-leucine and L-valine. Such mutants are sometimes referred to in the scientific literature as ilvE mutants. In practice, single colonies growing on an M9 salts glucose-based agar medium supplemented with all the individual amino acids found in casamino acid are transferred to a similar medium but which lacks L-isoleucine, L-leucine and L-valine. Colonies that require all three amino acids, L-isoleucine, L-leucine and L-valine, for growth but cannot grow in the presence of any two of such amino acids are considered to be branched-chain amino acid transaminase negative (ilvE), which can be verified by biochemical assays well known to those skilled in the art.

Those mutants used herein for genetic recombination and which are characterized by their lack of branched-chain 2-oxo acid biosynthetic activity are selected from mutagenized colonies on the basis of their inability to grown in a medium which lacks L-isoleucine and L-valine. Such mutants, not also demonstrating an L-leucine requirement, are also referred to herein as early ilv mutants. In practice, single colonies growing on an M9 salts glucose-based agar medium supplemented with all the individual amino acids found in casamino acids are transferred to a similar medium but which lacks L-isoleucine and L-valine. Such mutants do not require L-leucine for growth.

The strain or strains of *S. avermitilis* which are mutagenized and which mutants are selected for lack of branched-chain amino acid transaminase activity or branched-chain 2-oxo acid biosynthetic activity can themselves be mutants of *S. avermitilis* lacking, for example, avermectin B-O-methyl transferase activity. Alternatively, either or both of such mutants which lack branched-chain amino acid transaminase activity or branched-chain 2-oxo acid biosynthetic activity can be mutagenized and mutants thereof selected which are deficient in avermectin B-O-methyl transferase activity. Mutants lacking avermectin B-O-methyl transferase activity are unable to methylate the C-5 oxygen of the aglycone moiety of avermectins. Mutants lacking such activity produce essentially only B avermectins by preventing production of A avermectins and can be so identified. Such mutants are preferred.

Mutants of *S. avermitilis* characterized by their lack of branched-chain amino acid transaminase activity and branched-chain 2-oxo acid biosynthetic activity and, optionally, their lack of avermectin B-O-methyl transferase activity, also referred to herein as O-methyl transferase activity, can be produced by genetic recombination between mutants which lack branched-chain amino acid transaminase activity and, optionally, avermectin B-O-methyl transferase activity and mutants which lack branched-chain 2-oxo acid biosynthetic activity and, optionally, avermectin B-O-methyl transferase activity.

It was surprising and unexpected that the herein-described mutants lacking branched-chain 2-oxo acid biosynthetic activity and branched-chain amino acid transaminase activity retained the ability to produce natural avermectins and, especially, non-natural avermectins by incorporating exogenously supplied branched-chain 2-oxo acid precursors or branched-chain fatty acid precursors or compounds convertible thereto.

The present invention also includes any organism, regardless of its appearance or physiological behavior, that may be developed by means of transformation, transduction, genetic recombination or some other genetical procedure, using a nucleic acid or an equivalent material from the herein described species, whereby it has acquired the characteristics of the herein described mutants.

The terms "avermectin" or "avermectins" as used herein refer to compounds having formula (I), below, but wherein the 25-substituent (R) can be any group assimilable at said position by the *S. avermitilis* of this invention.

The herein described mutants are highly valuable for producing non-natural avermectins by the processes disclosed and exemplified herein. They are especially valuable for production of preferred avermectins, i.e., compounds wherein the C-25 substituent is $C_4$–$C_6$, with particularly preferred avermectins having a cyclohexyl substituent at the C-25 position and a particularly preferred avermectin being B1 avermectin with a cyclohexyl substituent at the C-25 position.

DETAILED DESCRIPTION OF THE INVENTION

Production of strains of *S. avermitilis* which lack branched-chain amino acid transaminase activity (ilvE) and branched-chain 2-oxo acid biosynthetic activity ("early ilv") useful in the process of this invention was accomplished by protoplast fusion between two appropriate mutants. Nonetheless, it is to be understood that such mutants can be prepared by other means well known to those skilled in the art. Such other means include but are not limited to mutation and genetic engineering with appropriate vectors.

Mutation of an avermectin-producing member of the species *Streptomyces avermitilis* is carried out according to known procedures using any of a variety of mutating agents including ultraviolet irradiation, X-ray irradiation, N-methyl-N'-nitro-N-nitrosoguanidine, ethylmethane sulfonate, nitrous acid and nitrogen mustards, e.g., N-methylbis(2-chloroethyl)amine, or like treatments. The mutagenesis can be conducted on spores or on a vegetative culture of *S. avermitilis* capable of producing natural avermectins, e.g., *S. avermitilis* ATCC 31272.

Mutagenized colonies are selected for lack of branched-chain amino acid transferase activity on the basis of their failure to grow on M9/glucose minimal plates except in the presence of L-isoleucine, L-leucine and L-valine. All three amino acids must be present for growth to occur. Further, it has been demonstrated that said transaminase negative mutants do not grow on media supplemented with all three of the 2-oxo acids which serve as substrates for the transaminase reactions. A single transaminase enzyme thus appears to catalyze transamination of each of the three 2-oxo acids (2-oxo-3-methyl valeric acid, 2-oxo-isocaproic acid, 2-oxo-isovaleric acid).

Mutagenized colonies are selected for lack of branched-chain 2-oxo acid biosynthetic activity on the basis of their failure to grow on M9/glucose minimal plates in the absence of isoleucine and valine. In the presence of isoleucine and valine, such mutants will grow on M9/glucose minimal plates.

In addition to production of desired alleles of a given strain of microorganism by mutagenesis, protoplast fusion permits introduction of desirable alleles produced/identified in one strain into the chromosome of another strain. For example, a strain of *S. avermitilis* deficient in branched-chain 2-oxo acid dehydrogenase activity and branched-chain amino acid transaminase activity can, by protoplast fusion with a *S. avermitilis* strain lacking branched-chain 2-oxo acid biosynthetic and O-methyl transferase activities produce a strain of *S. avermitilis* deficient in branched-chain 2-oxo acid biosynthetic, branched-chain amino acid transaminase and O-methyl transferase activities. As those skilled in the art recognize, protoplast fusion technology enables combination of desirable alleles from divergent lines of selection into a single strain. The herein described *S. avermitilis* 209R38 (ATCC 55220), a branched-chain 2-oxo acid biosynthesis, branched-chain amino acid transaminase and O-methyl transferase deficient strain, was produced via this technology.

The morphological and cultural characteristics of the mutants of this invention are generally as described in U.S. Pat. No. 4,429,042, the teachings of which are incorporated herein by reference. The distinguishing characteristic of the mutants of this invention are their lack of branched-chain 2-oxo acid biosynthetic activity, and branched-chain amino acid transaminase activity and O-methyl transferase activity which characteristics are determined as described herein.

*Streptomyces avermitilis* 209R38, also referred to as FD 28857, has been deposited under the terms of the Budapest Treaty in the American Type Culture Collection, Rockville, Md., a recognized depository affording permanence of the deposits and ready accessibility thereto by the public if a patent is granted on this application. It has been given the designation *Streptomyces avermitilis* ATCC 55220. The deposit is available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganism deposited will be irrevocably removed on Feb. 9, 1993 or upon granting of a patent requiring the microorganism for carrying out the claimed invention, whichever date is earlier.

Each of *S. avermitilis* ATCC 31267, ATCC 31271, ATCC 31272 and NCIB 12121 produces the natural avermectins, compounds of formula (I)

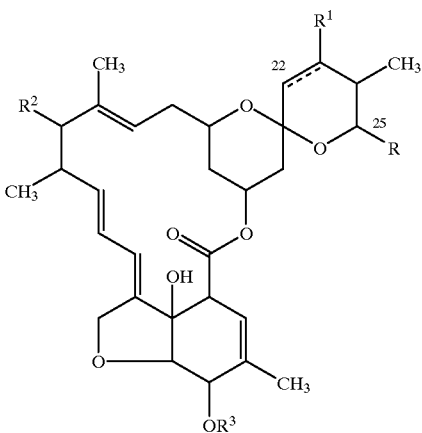

(I)

wherein the broken line at the 22–23 position represents an optional double bond;

$R^1$ is hydroxy and is present only when the double bond is absent;

$R^2$ is 4'-(alpha-L-oleandrosyl)-alpha-L-oleandrosyloxy of the formula

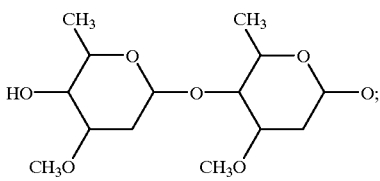

$R^3$ is hydrogen or methyl; and

R is isopropyl or (S)-sec-butyl.

U.S. Pat. No. 4,285,963 describes avermectins of the formula (I) wherein the 25-position is disubstituted with a methyl and an ethyl group; $R^1$ is hydroxy and $R^3$ is methyl.

In the non-natural avermectins referred to herein, R is a substituent other than isopropyl or (S)-sec-butyl and is defined below.

The compounds essential for utilization in the biosynthesis of formula (I) compounds occur in the cell of *S. avermitilis*. These compounds, L-valine and L-isoleucine, are believed to enter into the biosynthesis of avermectins via conversion to 2-oxo acid and decarboxylation of the acid by branched chain 2-oxo acid dehydrogenase, concomitant with coupling the product with coenzyme A. Their presence accounts for the concurrent production of both the isopropyl and (S)-sec-butyl compounds of the formula (I). This, of course, gives rise to problems in separating the isopropyl from the (S)-sec-butyl derivatives.

When fermented in a nutrient medium containing the appropriate primer compound, the mutants of this invention produce a compound of formula (I) or, as is more usually the case, a mixture of two or more compounds of formula (I) in which R corresponds to the primer compound used. Up to four products, conveniently and trivially referred to as R-avermectin A1, A2, B1 and B2, according to the designations used in U.S. Pat. No. 4,429,042, can be produced. The "R-" group, of course, refers to the C-25 substituent. For example, when R is cyclohexyl the four possible avermectins are:

| Trivial Name | $R^1$ | $R^3$ |
|---|---|---|
| cyclohexyl avermectin A1 | double bond | $CH_3$ |
| cyclohexyl avermectin A2 | hydroxy bond | $CH_3$ |
| cyclohexyl avermectin B1 | double bond | H |
| cyclohexyl avermectin B2 | hydroxy bond | H |

In the non-natural avermectins, the C-25 substituent "R" of formula (I) is other than isopropyl or (S)-sec-butyl.

Compounds of formula (I) wherein the double bond is present and OH is absent may alternatively be prepared from the corresponding compound of the formula (I) wherein $R^1$ is OH and the double bond is absent by a dehydration reaction. For example, the reaction is performed by first selectively protecting the hydroxy groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335, the teachings of which are incorporated herein by reference.

Formula (I) compounds wherein $R^3$ is H may also be prepared from the corresponding compounds wherein $R^3$ is $CH_3$ by demethylation. This reaction is achieved by treating the 5-methoxy compound, or a suitably protected derivative thereof, with mercuric acetate and hydrolyzing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209, the teachings of which are incorporated herein by reference.

Compounds of formula (I) wherein $R^1$ is H and the double bond is absent (so called dihydro avermectins) can be prepared from the corresponding compound wherein the double bond is present and $R^1$ is absent, by selective catalytic hydrogenation using an appropriate catalyst. For example, the reduction may be achieved using tris (triphenylphosphine) rhodium (I) chloride as described in European Patent Application Publication No. 0001689, and its counterpart U.S. Pat. No. 4,199,569, the teachings of which are incorporated herein by reference.

The compounds of formula (I) wherein $R^2$ is H are prepared from the corresponding compounds wherein $R^2$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone having a hydroxy group at the 13-position; this is then halogenated, for example by reaction with a benzene sulfonyl halide, to yield the 13-deoxy-13-halo derivative which is finally selectively reduced, for example using tributyltin hydride. In order to avoid unwanted side reactions, it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European Patent Application Publication No. 0002615.

The compounds capable of utilization by the S. avermitilis of this invention for the biosynthesis of avermectins, natural and non-natural, are compounds of formulae (II-A) and (II-B),

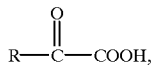
R—COOH and    (II-A)

(II-B)

including compounds convertible to (II-A) and (II-B) during the fermentation process. Said compounds are also referred to herein as "primer compounds".

More specifically, R, which becomes the C-25 substituent, is R' or —CH$_2$R". R' is an alpha-branched C$_3$–C$_8$ alkyl, alkenyl, alkynyl, alkoxyalkyl or alkylthioalkyl group; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methylene or one or more C$_1$–C$_4$ alkyl groups or halo atoms (fluoro, chloro, iodo or bromo); or a 3 to 6 membered oxygen or sulfur containing heterocyclic, ring which may be saturated, or fully or partially unsaturated and which may optionally be substituted by one or more C$_1$–C$_4$ alkyl groups or halo atoms.

R" is H, C$_1$–C$_8$ alkyl, C$_2$–C$_8$ alkenyl, C$_2$–C$_8$ alkynyl, alkoxyalkyl or alkylthioalkyl containing from 1 to 6 carbon atoms in each alkyl or alkoxy group, wherein any of said alkyl, alkoxyalkenyl or alkynyl groups may be substituted by one or more halo atoms; or a C$_3$–C$_8$ cycloalkyl or C$_5$–C$_8$ cycloalkenyl group, either of which may be substituted by methylene or one or more C$_1$–C$_4$ alkyl groups or halo atoms; or a 3 to 6 membered oxygen or sulphur containing heterocyclic ring which may be saturated, or fully or partially unsaturated and which may be substituted by one or more C$_1$–C$_4$ alkyl groups or halo atoms; or a group of the formula SR$^7$ wherein R$^7$ is C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, phenyl or substituted phenyl wherein the substituent is C$_1$–C$_4$ alkyl, C$_1$–C$_4$ alkoxy or halo, or a 3 to 6 membered oxygen or sulphur containing heterocyclic ring which may be saturated, or fully or partially unsaturated and which may be substituted by one or more C$_1$–C$_4$ alkyl groups or halo atoms. In the foregoing definition of R", alkyl groups containing 3 or more carbon atoms may be straight or branched chain.

Compounds convertible to RCOOH when R is R'; i.e., precursor in the fermentation process, are compounds of formula (II-C) wherein R' is as defined above:

R'(CH$_2$)$_n$—Z    (II-C)

wherein n is 0, 2, 4 or 6; and Z is —CH$_2$OH, —CHO, —CH$_2$NH$_2$, —COOR$^5$ or —CONHR$^6$ wherein R$^5$ is H or (C$_1$–C$_6$)alkyl; R$^6$ is hydrogen, (C$_1$–C$_4$)alkyl, or the residue of an amino acid, especially of aspartic acid, glutamic acid and methionine, e.g., —CH(COOH)CH$_2$COOH, —CH(COOH)(CH$_2$)$_2$COOH and —CH(COOH)(CH$_2$)$_2$SCH$_3$, respectively.

Compounds convertible to RCOOH where R is —CH$_2$R"; i.e., precursors in the fermentation process, are compounds of the formula (II-D) wherein R" is as defined above:

R"—(CH$_2$)$_n$—Z'    (II-D)

wherein Z' is —CH$_2$OH, —CH$_2$NH$_2$, —COOH or —CHO; n is 1, 3 or 5 when Z' is —CH$_2$OH, —CH$_2$NH$_2$ or —CHO and n is 3 or 5 when Z' is —COOH.

Compounds convertible to

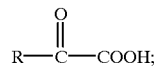
R—C—COOH;

i.e., precursors in the fermentation process, are compounds of the formula (II-E) wherein R and Z are as defined above:

(II-E)

Also included in this invention are the isomeric forms of formulae (II-A) and (II-B) compounds, and compounds convertible thereto during the fermentation process, and the isomeric avermectins at C-25 resulting from their use in the herein described process.

The process of this invention is carried out by aerobically fermenting a strain of S. avermitilis which lacks branched-chain 2-oxo acid biosynthetic activity, branched-chain amino acid transaminase activity, and, optionally and preferably, O-methyl transferase activity in an aqueous nutrient medium comprising an assimilable source of nitrogen, carbon, inorganic salts and a compound of formula RCOOH, RCOCOOH or a compound convertible to said compound (i.e., a precursor) during the fermentation. The acid, or compound convertible thereto, is added to the fermentation either at the time of inoculation and/or at intervals during the fermentation. The medium must contain L-isoleucine, L-leucine and L-valine in order for growth of the mutant to occur. Production of the avermectin products may be monitored by removing samples from the fermentation, extracting with an organic solvent and following the appearance of the product by chromatography, for example, using high performance liquid chromatography. Incubation is continued until the yield of the product has been maximized, generally for a period of from 4 to 21 days.

A preferred level of each addition of the primer compounds when R is R' (carboxylic acid or compound convertible thereto) is between 0.05 and 3.0 grams per liter. A preferred level of each addition of the primer compounds when R is —CH$_2$R" (carboxylic acid or compound convertible thereto) is between 0.05 and 4.0 grams per liter with the best yields obtained by gradually adding the primer compound to the fermentation, for example, by daily additions thereof over a period of several days. The primer compound can be added continuously, intermittently or all at once to the fermentation. The acid (RCOOH or RCOCOOH) is added as such or as a salt, such as the sodium, lithium or ammonium salt, or as a compound convertible to the acid as defined above. The acid, if a solid, is preferably dissolved in a suitable solvent such as water or (C$_1$–C$_4$)alcohols.

The media used for the fermentation can, especially when the C-25 substituent is to be isopropyl or (S)-sec-butyl, be conventional media containing assimilable sources of carbon, nitrogen and trace elements. When the C-25 substituent is to be a non-natural group; i.e., it is not isopropyl or (S)-sec-butyl, the fermentation medium is one in which the chosen ingredients lack, or contain only minimal amounts of primer compounds wherein the R moiety is isopropyl or (S)-sec-butyl.

After fermentation for a period of several days at a temperature preferably in the range of 24 to 33° C., the fermentation broth is centrifuged or filtered and the mycelial cake is extracted with a solvent, preferably acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product is further purified as necessary, for instance by crystallization and/or chromatography as for example by using preparative reverse phase, high performance liquid chromatography.

The crude product is generally obtained as a mixture of the compounds of formula (I) wherein $R^2$ is 4'-(alpha-L-oleandrosyl)-alpha-L-oleandrosyloxy, $R^1$ is OH and the double bond absent or $R^1$ is absent and the double bond is present and wherein $R^3$ is H or $CH_3$; however, the proportions can vary depending on the particular mutant and primer compound employed and the conditions used.

The source of the R group; i.e., whether it comes directly from R—COOH or R—COCOOH, or is produced from one of the above precursors, or from any precursor, is immaterial to the production of the avermectins. The critical requirement of the process of this invention for their production is that the desired R group be made available to the *S. avermitilis* strains of this invention in the fermentation process.

Suitable primer compounds include the following:
2,3-dimethylbutyric acid
2-methylhexanoic acid
2-methylpent-4-enoic acid
2-cyclopropyl propionic acid
4,4-difluorocyclohexane carboxylic acid Lithium salt
4-methylenecyclohexane carboxylic acid
3-methylcyclohexane carboxylic acid (cis/trans)
1-cyclopentene carboxylic acid
1-cyclohexene carboxylic acid
tetrahydropyran-4-carboxylic acid
thiophene-2-carboxylic acid
3-furoic acid
2-chlorothiophene-4-carboxylic acid
cyclobutane carboxylic acid
cyclopentane carboxylic acid
cyclohexane carboxylic acid
cycloheptane carboxylic acid
2-methylcyclopropane carboxylic acid
3-cyclohexene-1-carboxylic acid
2-methylthiopropionic acid
2-methyl-4-methoxybutyric acid
thiophene-3-carboxylic acid
hydroxymethylcyclopentane
3-thiophene carboxaldehyde
3-cyclohexylpropionic acid
3-cyclopentylpropionic acid
hydroxymethylcyclobutane
tetrahydrothiophene-3-carboxylic acid
3-cyclopentyl-1-propanol
3-methylcyclobutane carboxylic acid Lithium salt
3-fluorocyclobutane carboxylic acid
3-methylenecyclobutane carboxylic acid Lithium salt
2-methyl-4-methylthiobutyric acid
tetrahydrothiopyran-4-carboxylic acid
cyclobutylmethylamine
ethyl cyclobutanecarboxylate
4-hydroxymethylcyclopentene
2-(3-thiophenecarbonyl)propionic acid ethyl ester
(S)-2-methylpentanoic acid
(R)-2-methylpentanoic acid
methylthioacetic acid
ethylthioacetic acid
3-methylbutyric acid
3-trifluoromethyl butyric acid
3-methylpentanoic acid
n-butyric acid
cyclopentane acetic acid
thiophene-3-acetic acid
propionic acid.

O-methyl transferase mutants can be obtained from the herein-described branched-chain 2-oxo acid biosynthetic negative and branched-chain amino acid transaminase negative mutants. Mutants which lack branched-chain 2-oxo acid biosynthetic activity, branched-chain amino acid transaminase activity and O-methyl transferase activity, when fed RCOOH or RCOCOOH compounds, or compounds convertible thereto during the fermentation process, produce primarily B avermectins, demethylavermectins or demethylavermectin B compounds. Said mutants can be obtained, for example, by mutagenesis of the herein described mutants which lack branched-chain 2-oxo acid biosynthetic activity and branched-chain amino acid transaminase activity by means of ultraviolet light and/or chemical mutagens such as N-methyl-N-nitrosourethan, N-methyl-N'-nitro-N-nitrosoguanidine, ethyl methane sulfonate or other agent such as those enumerated above. Alternatively, branched-chain 2-oxo acid biosynthetic positive strains and/or branched-chain amino acid transaminase positive strains which lack O-methyl transferase activity can be mutated by treatment with UV light or a mutagenizing agent to produce the branched-chain 2-oxo acid biosynthetic negative mutants and/or branched-chain amino acid transaminase negative mutants which also lack O-methyl transferase activity. Preferably, a mutant lacking O-methyl transferase activity is further mutated to obtain a mutant lacking both O-methyl transferase activity and branched-chain 2-oxo acid biosynthetic activity. Such a mutant can then be used as one parent in fusion with a mutant lacking branched-chain amino acid transaminase activity.

The non-natural avermectins produced by such mutants are characterized by the presence of hydroxy groups at the C-5 position of the aglycone moiety and/or the C-3' and/or C-3" positions of the oleandrose moieties.

The above-described mutants are identified according to the methodology described by Schulman et al. Antimicrobial Agents and Chemotherapy, 29, 620–624 (1986). They are useful for the same purposes and in the same way as are the known avermectins.

Alternatively, increased amounts of the B avermectins, including those lacking methyl groups on the oleandrose disaccharide moiety, are produced by fermenting the mutants of this invention, which lack branched-chain 2-oxo acid biosynthetic and branched-chain amino acid transaminase activities, in the presence of a substance such as sinefungin, S-adenosyl-ethionine or S-adenoyslhomocysteine which inhibits O-methyl transferase activity.

The compounds of this invention are highly active antiparasitic agents having particular utility as anthelmintics, ectoparasiticides, insecticides and acaricides.

Thus, the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trinchinella, Capillaria, Trichuris, Enterobius and parasites which are found in the blood or other tissues and organs such as filarial worms and the extract intestinal states of Strongyloides and Trichinella.

The compounds are also of value in treating ectoparasite infections including, in particular, arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or a liquid drench, or alternatively, they may be administered by injection or as an implant. Such formulations are prepared in a conventional manner in accordance with standard veterinary practice. Thus, capsules, boluses or tablets may be prepared by mixing the active ingredient with a suitable finely divided diluent or carrier additionally containing a disintegrating agent and/or binder such as starch, lactose, talc, magnesium stearate etc. A drench formulation may be prepared by dispersing the active ingredient in an aqueous solution together with dispersing or wetting agents, etc., and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally, for oral administration a dose of from about 0.001 to 10 mg per kg of animal body weight given as a single dose or in divided doses for a period of from 1 to 5 days will be satisfactory, but, of course, there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests, the compounds are applied as sprays, dusts, emulsions and the like in accordance with standard agricultural practice.

The following Examples are illustrative of this invention and are not to be construed as limiting the scope of the invention in any way.

EXAMPLE 1

Construction of S. avermitilis ATCC 55220 (F.D. 28857) Lacking Branched-chain Amino Acid Transaminase Activity, Branched-chain 2-oxo Acid Biosynthetic Activity and O-methyl Transferase Activity A. Construction of S. avermitilis Mutant I-3 (ATCC 53567) Lacking Branched-chain 2-oxo Acid Dehydrogenase Activity Mutant I-3 (ATCC 53567) was prepared as described in European patent application publication no.284,176, published Sep. 28, 1988. For completeness, that disclosure is repeated immediately below.

Step 1

S. avermitilis ATCC 31272 was grown as a confluent lawn on New Patch Agar Medium for 12 days at 30° C. The medium comprised

| V-8 Juice* | 200 ml |
|---|---|
| CaCO$_3$ | 3 grams |
| Agar | 15 grams |
| H$_2$O to | 1000 ml |
| Nutrient broth | 1.0 grams/L |
| sodium acetate 3H$_2$O | 1.4 grams/L |
| isovaleric acid | 50 mg/L |
| isobutyric acid | 50 mg/L |
| 2-methylbutyric acid | 50 mg/L |
| isoleucine | 250 mg/L |
| leucine | 250 mg/L |
| valine | 250 mg/L |
| trace elements solution** | 1 ml/L |

*A mixture of 8 vegetable juices (tomato, carrots, celery, beets, parsley, lettuce, watercress and spinach) plus salt, ascorbic and citric acids and natural flavors. Available from Campbell Soup Company, Camden, NJ.
**Composition of Trace elements solution:

| FeCl$_3$.6H$_2$O | 2.7 g |
|---|---|
| MnSO$_4$.H$_2$O | 4.2 |
| CuSO$_4$.5H$_2$O | 0.5 |
| CaCl$_2$ | 11.0 |
| H$_3$BO$_3$ | 0.62 |
| CoCl$_2$.6H$_2$O | 0.24 |
| ZnCl$_2$ | 0.68 |
| Na$_2$McO$_4$ | 0.24 |

Dissolve the above in 1 liter of 0.1N HCl.

Spores were harvested from 3 such plates and suspended in 20 ml of 0.05M trismaleic acid buffer, pH 9.0.

Step 2

10 ml of the spore suspension was added to a vial containing 10 mg of N-methyl-N'-nitro-N-nitrosoguanidine (NTG). The vial was incubated and shaken at 28° C. for 60 minutes and the spores then washed profusely with 1% NaCl solution.

Step 3

The washed spores were suspended in 1% NaCl and mixed with an equal volume of 80% ethylene glycol. This suspension was preserved at −20° C. and used as a source of cells to be screened for mutants. It gave approximately $10^4$ colonies/ml when germinated.

This spore stock was spread on YPD plates to yield approximately 100 colonies per plate (YPD medium comprises 10 g/l of each of yeast extract, Baco peptone* and dextrose; and 15 g/l of Bacto agar*, adjusted to pH 6.9 before autoclaving). Ingredients marked with an asterisk are available from Difco Laboratories, Detroit, Mich. 48238.

Step 4

Single colonies were picked from plates after 2–3 weeks of growth at 28° C. and placed in individual wells of a standard 96 well microtiter plate. Also, a small quantity of the colony was patched onto a fresh agar medium to serve as a source of viable cells when mutants are identified.

Step 5

To each well was added approximately 75 microliters of a liquid M9 salts medium containing 1% glucose, 0.1% casamino acids, and 0.01% of each of isovaleric, isobutyric and 2-methylbutyric acids. After several days of incubation at 28° C., the cells were assayed for the presence of branched-chain 2-oxo acid dehydrogenase. (Each liter of M9 salts medium comprises 6 g Na$_2$HPO$_4$, 3 g KH$_2$PO$_4$, 0.5 g NaCl and 1 g of NH$_4$Cl. The medium is autoclaved and then 1 ml each of sterilized 1M $MgSO_4$ and 0.1M $CaCl_2$ are added aseptically).

Step 6

A microsuspension of 5% toluene in M9 salts medium was prepared by a brief sonication of the immiscible mixture. To 25 ml of this suspension was added 1.2 ml of a solution containing [$^{14}$C-1]-2-oxo-isocaproic acid, 2.5 microcurie/ml and 10.0 microcurie/micromole. 50 Microliters of this overall mixture was added to each of the wells of the microtiter plates containing the colonies to be assayed.

Step 7

The $^{14}CO_2$ produced from each well was trapped and visualized by the procedure described by Tabor et al., *J. Bacteriol.* 128 485–486 (1976) entitled "Convenient Method for Detecting $^{14}CO_2$ in Multiple Samples: Application to Rapid Screening for Mutants". Mutants lacking active branched-chain 2-oxo acid dehydrogenase produce no $Ba^{14}CO_3$ beyond that observed for the controls.

A more refined method which improves the contrast between a positive assay for $^{14}CO_2$, indicated by a dark spot on the autoradiogram as a result of $Ba^{14}CO_3$ formation, and a negative assay indicated by no spot or a very light spot, comprises the following modified screen:

Single colonies (see Step 4 above) were picked from the agar medium after 7–14 days of growth (rather than 2–3 weeks) and assayed directly by steps 6 and 7 above. Step 5 of the above procedure is omitted.

An even more refined assay method which is quantitative in nature as regards $^{14}CO_2$ release comprises growing the mutants detected by the above screens on a suitable medium comprising M9 salts medium with glucose, 1% and "Syncasa-bcaa", 0.1% (a synthetic mixture of L-amino acids with the approximate composition of commercial casamino acids, but without the presence of L-valine, L-isoleucine and L-leucine, see below).

After growth to high cell density, the cells were washed in M9 salts medium and resuspended in cold M9 salts medium containing 1% toluene which had been sonicated to produce a milky white dispersion of the toluene. The cell/buffer/toluene suspension was incubated for 40 minutes at 30° C. in order to permeabilize the cells. The permeabilized cells were then washed in M9 medium salts and finally resuspended in one-fifth the original volume of M9 medium buffer. 180 Microliters of this suspension were used per assay.

A reaction volume of 300 microliters contained the toluenized cells, thiamine pyrophosphate (TPP), 0.4 mM; coenzyme A (CoA), 0.11 mM; nicotinamide adenine dinucleotide (NAD), 0.68 mM; dithiothreitol (DTT), 2.6 mM; $MgCl_2$, 4.1 mM; Tris-HCl, 60 mM, pH 7.5; and [$^{14}$C-1]2-oxoisocaproate, 6,000 cpm, microcurie per micromole. The efficiency of counting was 73%. The reaction was carried out in 15 ml scintillation vials containing a 2×2 cm Whatman #4 paper square pressed into the screw cap of the vial. The paper contains 30 microliters of 1M Hyamine Hydroxide (1M solution of methylbenzethonium hydroxide in methanol; available from Sigma Chemical Co., St. Louis, Mo. 63178), which traps $^{14}CO_2$ evolved in the reaction. After incubation for 2 hours, the papers are immersed in 10 ml of Beckman Aquasol II (Universal LSC (liquid scintillation counter) available from New England Nuclear Research Products, Boston, Mass. 02118) and the radioactivity measured in a liquid scintillation counter after equilibration in this solvent for 4 hours or more. A blank control reaction (i.e., —no cells) gives ca. 50–300 cpm.

Mutant I-3 and others like it gave counts that were less than or equal to the blank control reaction, whereas the parent strain gave counts several fold higher than the blank control value.

B. Construction of *S. avermitilis* Mutant 2369 Lacking Branched-chain 2-oxo Acid Dehydrogenase and O-methyl Transferase Activities Spores of mutant I-3 were subjected to mutagenesis using NTG in accordance with the procedure described in Part A, above. Following mutagenesis, the spores were spread for single colony isolates (about 30 colonies per plate) on YPD agar of the following composition:

| Yeast Extract | 10 g |
|---|---|
| Bactopeptone | 10 g |
| Dextrose | 5 g |
| Bactoagar | 15 g |
| $H_2O$ | 1 L | pH ~ 6.9, autoclaved at about 121° C. for 20 mins.

The plates were incubated at about 34° C. for 7 days. Then, single colonies were picked, using sterile flat toothpicks, from the YPD plates and spread as patches onto AP5/MB quadrant plates which had been prepared as described below.

AP5/MB Production Agar:

| Thinned starch | 180 ml |
|---|---|
| $K_2HPO_4$ | 1 g |
| $MgSO_4 \cdot 7H_2O$ | 1 g |
| Ardamine PH | 5 g |
| $CaCO_3$ (marblewhite) | 5 g |
| P-2000 | 1 ml |
| $FeSO_4 \cdot 7H_2O$ | 0.01 g |
| $MnCl_2 \cdot 4H_2O$ | 0.001 g |
| $ZnSO_4 \cdot 7H_2O$ | 0.001 g |
| Bactoagar | 17 g |
| $H_2O$ | 795 ml | pH ~ 7.0, autoclaved at about 121° C. for 20 mins. Following autoclaving, 20 ml of filter sterilized 5% stock solution of methylbutyric acid was added to the agar by sterile technique. Then, the quadrant petri dishes were filled with the agar.

Onto each patch was placed a sterile 20 mm diameter Reemay #2250 membrane (Ahlstrom Filtration, Mount Holly Springs, Pa., U.S.A.) which had been autoclaved in distilled water at about 121° C. for 1.5 hours. The plates were then incubated at about 28° C. for 9 days.

On day 9, the membranes were removed from the colony patches using sterile forceps and placed in glass scintillation vials. To each vial were added 250 µl of acetone followed by gentle shaking. The vials were capped until the next step.

To assay the acetone extracts of each colony obtained as described above, 20 µl of each extract were spotted onto Analtech 250 micron TLC plates (Analtech Inc., Newark, Del., U.S.A.). The plates were placed in chromatography tanks containing ether and chromatographed for 25 mins. Then, the plates were removed and air-dried. To visualize the products, the plates were sprayed with 3% vanillin in 3A ethanol and placed in a drying oven at 95–100° C. for 3–5 mins. Then, the plates were sprayed with 3% $H_2SO_4$ in 3A ethanol. The plates were screened to find colonies which produced B1a and B2a but did not produce avermectin A1a and A2a, i.e., lacked O-methyl transferase. Mutant 2369, when purified by single colony isolation, was identified as a strain which produced B1a and B2a, and little or no A1a and A2a.

C. Isolation of *S. avermitilis* Mutant 7881 Lacking Branched-chain 2-oxo Acid Dehydrogenase Activity and O-methyltransferase Activity and Producing Higher Titers of Avermectin B Compounds Strain 7881 was obtained from mutant 2369 after NTG mutagenesis as follows. Spores of mutant 2369 were subjected to mutagenesis with NTG in accordance with the procedure described in Part A, above. Following mutagenesis, the spores of strain 2369 were spread for single colonies on YPD agar. Mutagenized colonies were taken from the YPD agar plates and used to inoculate 300 ml Erlenmeyer flasks containing 30 ml of AS-7 medium. The flasks were incubated with shaking at 28–30° C. and 200 rpm for about 40 hours. Then, 2.5 ml of the cultures were used to inoculate flasks containing 30 ml of AP-5 medium with S(+)-2-methylbutyrate at 400 ppm in 300 ml Erlenmeyer flasks. The flasks were incubated with shaking at 28–30° C. and 200 rpm for 13–20 days. The cultures were then extracted with solvent and anlayzed for avermectin production according to the HPLC procedure described below.

The AS-7 medium and the AP-5 medium are composed as follows.

| AS-7 Medium | |
| --- | --- |
| | g/L |
| thinned starch [a] | 20 |
| Ardamine pH [b] | 5 |
| Pharmamedia [c] | 15 |
| CaCo$_3$ | 2 |

[a] Prepared by hydrolysis of starch by alphaamylase from *Bacilius licheniformis* (available from Novo Enzymes, Wilton, CT and sold under the trademark "Termamyl") to a dextrose equivalent of 40% ± 5%.
[b] From Yeast Products, Inc., Clifton, NJ 07012
[c] From Traders Protein, Memphis, TN 38108

Adjust pH to 7.2 with NaOH.

| AP-5 Medium | |
| --- | --- |
| | g/l |
| thinned starch | 80 |
| Ardamine pH | 5 |
| K$_2$HPO$_4$ | 1 |
| MgSO$_4$.7H$_2$O | 1 |
| NaCl | 1 |
| CaCO$_3$ | 7 |
| FeSO$_4$.7H$_2$O | 0.01 |
| MnCl$_2$.7H$_2$O | 0.001 |
| ZnSO$_4$.7H$_2$O | 0.001 |
| P-2000 (antifoam) | 1 ml/l |

General High Performance Liquid

Chromatography (HPLC) Procedures

Mobile Phase
  120 ml of water
  70 ml of acetonitrile
  bring to 1 liter with methanol
Column
  Ultrasphere ODS 25 cm (Beckman Instruments, Fullerton, Calif. 92634-3100)
    flow: 0.75 ml/minute
    detection: UV at 240 nm
    attention: near 6
Sample diluent (D)
  35 ml acetonitrile plus 390 ml methanol
Standards
  1. weigh 0.5 mg avermectin A2a into 10 ml flask and bring to volume with methanol
  2. weigh 0.5 mg test product into 10 ml flask and bring to volume with methanol
1 and 2 are Standard Stock Solutions; For Standard Solution to Run
  take 100 µl (1) and 100 µl (2) into a vial
  add 800 µl mobile phase
Samples
  1. Take 1 ml of well shaken broth; spin down
  2. Remove as much supernatant as possible without disturbing pellet
  3. Add 100 µl of HPLC water to the pellet and vortex mix to disperse
  4. Add 2 ml diluent (D) and mix well
  5. Filter the same and run on HPLC.

The natural avermectins were subjected to this HPLC chromatographic procedure and the retention time of the peaks of the individual avermectins divided by the retention time observed for the oligomycin A present and which serves as internal standard for a given HPLC determination. Oligomycin A is almost always observed by HPLC as by-product of *S. avermitilis* fermentations and is a product seen on HPLC produced by the mutants described herein. Typically, oligoymycin A retention time is 9–10 minutes. The ratio of the retention times (RT) affords a more significant basis for comparing the identity and yields of avermectin products. The general order of appearance of the avermectin products on HPLC is B2, A2, B1 and A1.

| Natural Avermectin | RT/RT (oligomycin A) |
| --- | --- |
| B2b | 0.75 |
| B2a | 0.87 |
| A2b | 0.94 |
| A2a | 1.08 |
| B1b | 1.28 |
| B1a | 1.58 |
| A1b | 1.58 |
| A1a | 2.01 |

| Non-Natural Avermectin | RT/RT (oligomycin A) |
| --- | --- |
| cyclohexyl B2 | 1.18 |
| cyclohexyl B1 | 2.16 |
| cyclohexyl A2 | 1.48 |
| cyclohexyl A1 | 2.75 |

Retention times vary 1–2 minutes on different days, with oligomycin A generally appearing near 9–10 minutes.

Mutant 7881 was so identified as producing a higher titer of avermectin B compounds as compared to mutant 2369. In addition to the higher titer producing ability of 7881, it also lacks both branched-chain 2-oxo acid dehydrogenase activity and O-methyl transferase activity.

D. Construction of *S. avermitilis* Mutant 20-29 Lacking Both Branched-chain 2-oxo Acid Dehydrogenase and O-methyl Transferase Activities and Producing Higher Titers of Avermectin B Compounds The procedure described in Part C, above, was used with the exception that spores of mutant 7881 were mutated and mutant 20-29 was isolated. Mutant 20-29 lacks both branched-chain 2-oxo acid dehydrogenase and O-methyl transferase activities and produces a higher titer of avermectin B compounds than mutant 7881.

E. Isolation of *S. avermitilis* Mutant 49-40 Lacking O-methyl Transferase Activity During fermentation of mutant 20-29 a spontaneous mutant was identified due to its ability to produce natural avermectins in the absence of the addition of the appropriate branched-chain fatty acid precursor to the media. The mutant, identified as 49-40, was verified as having branched-chain 2-oxo acid dehydrogenase activity by using the $^{14}CO_2$ assay with permeabilized cells as described above. Mutant 49-40 lacks O-methyl transferase activity.

F. Construction of *S. avermitilis* Mutant 49-40H1 Lacking O-methyl Transferase Activity and Requiring Isoleucine and Valine For Growth ("Early ilv," Lacks Branched-chain 2-oxo Acid Biosynthetic Activity)

Strain 49-40 was subject to mutagenesis as follows.

Step 1

Strain 49-40, grown on a fresh SAMM agar plate for four days, as used to inoculate a 300 ml flask containing 50 ml of SCM medium (pH 7.2). The flask was then shaken at 200 RPM and 30° C. for twenty-four hours (final pH=8.2).

Step 2

The flask was removed from the shaker and 10 ml of the whole broth centrifuged in a sterile tube for five minutes at 2000 RPM. The cells were then resuspended in 50 ml of SCM medium in sterile 300 ml Erlenmeyer flasks and the flasks shaken on a rotary shaker for two hours at 30° C.

Step 3

The 10 ml of the suspension was placed in a sterile tube.

Step 4

Ethylmethane sulfonate (250 µl) was added to the tube (in a well ventilated hood), the contents thoroughly mixed, then poured into a sterile 300 ml flask and the flask shaken in a rotary shaker for three hours at 30° C.

Step 5

Fresh sterile SCM medium (40 ml) was added to the flask and shaking continued for a total of 70 hours at 30° C.

Step 6

The flask was removed, the contents spun down at 8000 RPM for ten minutes at 20° C. The cells were washed by re-suspending in SCM medium, spun down again and re-suspended in 10 ml SCM medium.

| SCM MEDIUM | |
|---|---|
| Yeast autolysate | 10 g/l |
| Beef Extract | 5 g/l |
| Casein enzymatic hydrolysate | 10 g/l |
| 1M MgSO$_4$ | 3 g/l |
| 1M K$_2$HPO$_4$; pH 7.0 (HCl) | 100 g/l |

| SAMM Agar Plate | |
|---|---|
| | g/L |
| Na$_2$HPO$_4$ | 6.0 |
| KH$_2$PO$_4$ | 3.0 |
| NaCl | 0.5 |
| NH$_4$Cl | 1.0 |

| -continued | |
|---|---|
| SAMM Agar Plate | |
| | g/L |
| 1M MgSO$_4$ | 1.0 |
| 0.1M CaCl$_2$ | 1.0 |
| Dextrose | 8.0 |
| Casamino Acids | 20.0 |
| Agar | 20.0 |

Following mutagenesis, the culture was spread for single colony isolates (about 150 per plate) on YPD agar and incubated at about 30° C. for about 5 days. Then, mycelia from each colony were replica plated onto M9 salts agar-based medium with glucose. The replica plates were incubated at 30° C. for 3 days. The plates were screened and a mutant which requires isoleucine and valine for growth was identified. The mutant, referred to as 49-40H1, lacks O-methyl transferase activity and has acquired an early ilv mutation causing it to require isoleucine and valine for growth.

G. Isolation of *S. avermitilis* Mutant 49-40H1ILV$^+$ Which Lacks O-methyl Transferase Activity, Requires Isoleucine and Valine for Growth ("Early ilv") and is Capable of Utilizing a Mixture of Isoleucine, Leucine and Valine as its Sole Carbon Sources (ILV$^+$)

Spores of mutant 49-40H1 were spread onto M9 minimal salts agar containing, as the sole carbon sources, a mixture of 0.33% each of isoleucine, leucine and valine. The plates were incubated at 30° C. and screened periodically for the appearance of colonies growing well amidst the lawns of poorly growing colonies of 49-40H1. The well-growing colonies were purified by streaking onto YPD agar plates and one such colony was designated 49-40H1ILV$^+$. Mutant 49-40H1ILV$^+$ lacks O-methyl transferase activity, requires isoleucine and valine for growth ("early ilv") but is capable of utilizing isoleucine, leucine and valine as its sole carbon sources (ILV$^+$).

H. Construction of *S. avermitilis* Mutant PGS-131 Which Lacks O-methyl Transferase Activity (omt$^-$), Requires Isoleucine and Valine for Growth ("Early ilv", Lacks Branched-chain 2-oxo Acid Biosynthetic Activity), is Capable of Utilizing a Mixture of Isoleucine, Leucine And Valine as Its Sole Carbon Sources (ILV$^+$) And Requires Arginine And Uracil For Growth (car-11)

Mutant 49-40H1ILV$^+$ was grown in SCM medium and subjected to mutagenesis using EMS according to the procedure described above in Part F. Following mutagenesis, the culture was diluted and spread for single colony isolates (about 150 per plate) on YPD agar. The plates were incubated at about 30° C. for 5 days. Then, mycelia from the single colony isolates were replica-plated onto M9 salts agar-based medium with leucine, isoleucine, and valine, each at 100 µg/ml, present. The plates were incubated at 30° C. for 3 days and then screened for colonies which do not grow. One such colony was identified and referred to as PGS-131. Mutant PGS-131 (omt$^-$, early ilv, ILV$^+$, car-11) lacks O-methyl transferase activity (omt$^-$), requires isoleucine and valine for growth ("early ilv", lacks branched-chain 2-oxo acid biosynthetic activity), is capable of utilizing a mixture of isoleucine, leucine and valine as its sole carbon sources (ILV⁺) and requires arginine and uracil for growth (tentatively designated car-11). PGS-131 was one of the parent strains used in the fusion described below to construct strain 209R38 (ATCC 55220).

I. Construction of S. avermitilis Mutant PGS-119 (ATCC 53670) Which Lacks Branched-chain 2-oxo Acid Dehydrogenase Activity and Branched-chain Amino Acid Transaminase Activity Mutant PGS-119 (ATCC 53670) was prepared as described in European patent application no. 284,176, published Sep. 28, 1988. For completeness, that disclosure is repeated immediately below.

Step 1

Approximately 100 mg of S. avermitilis I-3 (ATCC 53567), grown on a fresh SAMM agar plate for four days, was inoculated into a 300 ml flask containing 50 ml of SCM medium (pH 7.2). The flask was then shaken at 200 RPM and 30° C. for twenty-four hours (final pH=8.2).

Step 2

The flask was removed from the shaker and 10 ml of the whole broth centrifuged in a sterile tube for five minutes at 2000 RPM. The cells were then resuspended in 50 ml of SCM medium in sterile 300 ml Erlenmeyer flasks and the flasks shaken on a rotary shaker for two hours at 30° C.

Step 3

The 10 ml of the suspension was placed in a sterile tube.

Step 4

Ethylmethane sulfonate (250 μl) was added to the tube (in a well ventilated hood), the contents thoroughly mixed, then poured into a sterile 300 ml flask and the flask shaken in a rotary shaker for three hours at 30° C.

Step 5

Fresh sterile SCM medium (40 ml) was added to the flask and shaking continued for a total of 70 hours at 30° C.

Step 6

The flask was removed, the contents spun down at 8000 RPM for ten minutes at 20° C. The cells were washed by re-suspending in SCM medium, spun down again and re-suspended in 10 ml SCM medium.

Step 7

Cells were removed and assayed via replica plating, ca. 150 colonies/plate, for their ability to grow on M9/glucose minimal plates in the presence and absence of L-leucine, L-isoleucine, L-valine and combination of any of said amino acids. The mutant cells of interest grew only on media supplemented with L-leucine, L-isoleucine and L-valine. These derivatives of S. avermitilis I-3 (ATCC 53567), deficient in branched-chain amino acid transaminase activity, also failed to grow on media supplemented with one or more of the three 2-oxo acids (2-oxoisocaproic acid; 2-oxo-3-methylvaleric acid and 2-oxoisovaleric acid) which serve as precursors for L-leucine, L-isoleucine and L-valine. This behavior is completely opposite to that of S. avermitilis I-3 (ATCC 53567) which grew well on such media. Thus, a single transaminase enzyme appears to catalyze transamination of said 2-oxo acids.

Mutant PGS-119 (ATCC 53670) was so identified and lacks both branched-chain 2-oxo acid dehydrogenase activity and branched-chain amino acid transaminase activity.

J. Construction of S. avermitilis PGS-132 Lacking Both Branched-chain 2-oxo Acid Dehydrogenase Activity and Branched-chain Amino Acid Transaminase Activity, and Requiring Guanosine for Growth Spores of mutant PGS-119 (ATCC 53670) were subjected to mutagenesis with EMS according to the procedure described in Part I, above. Following mutagenesis, the mutagenized culture was spread for single colony isolates (about 150 per plate) (on YPD agar and incubated at about 0° C. for 5 days. Then, mycelia from the single colony isolates were replica plated onto M9 salts agar based medium with 0.5% glucose and leucine, isoleucine, and valine, 100 μg/ml each. The replica plates were incubated at about 30° C. for 3 days and then screened for mutants which do not grow. One such mutant, referred to as PGS-132 was identified. PGS-132 lacks both branch-chain 2-oxo acid dehydrogenase activity and branched-chain amino acid transaminase activity, and requires guanosine for growth (qua). PGS-132 was one of the parent strains used in the fusion described below to construct strain 209R38 (ATCC 55220).

K. Fusion of Mutant PGS 131 and PGS 132 and Isolation of S. avermitilis 209R38 (F.D. 28857, ATCC 55220)

To prepare protoplasts of PGS 131 and PGS 132 for fusion, cells of each strain were prepared as follows. Fresh cells, growing on YPD-4 agar were aseptically transferred by agar plug into AS-7 medium (40 ml) in 300 ml Erlenmeyer flasks. After one day of incubation at about 30° C., 200 rpm, 2.5 ml of each culture was transferred into 40 ml of AP-5 medium in 300 ml Erlenmeyer flasks. The flasks were incubated at about 30° C., 200 rpm for one day. Then 2.5 ml of the AP-5 medium grown culture was used to inoculate 50 ml of YEME medium in 300 ml baffled Erlenmeyer flasks. The flasks were incubated at about 30° C., 200 rpm for about two days.

The YPD-4 agar and YEME medium are composed as follows.

| YPD-4-Agar | |
| --- | --- |
| | g/L |
| Difco-Yeast Extract | 10 |
| Difco-Bacto Peptone | 10 |
| Dextrose | 5 |
| Na Acetate | 3 |
| Agar-[N-Morpholino]propanesulfonic acid ph to 7.0 with NaOH | 10<br>20 |
| Autoclave 25 min. @ 121° C., then add 3BCFA | 1.3 ml/L |

| 3BCFA | | |
| --- | --- | --- |
| (S)(+)-2-Methylbutyric acid | 5%, pH 7.2 (NaOH) | 10 ml |
| Isovaleric acid | 5%, pH 7.1 (NaOH) | 4 ml |
| Isobutyric acid | 5%, pH 7.1 (NaOH) | 12 ml |
| Mix well, filter sterilize. | | |

| YEME Medium | |
| --- | --- |
| Base solution: | |
| Difco yeast extract | 3 g |
| Difco Bacto-peptone | 5 g |
| Difco Bacto malt extract broth | 3 g |
| Glucose | 10 g |
| Sucrose | 300 g |

| -continued | |
|---|---|
| YEME Medium | |
| Distilled water to | 973 ml |
| Autoclave for 25 min. @ 121° C. | |
| After autoclaving, add sterile: | |
| MgCl$_2$.6H$_2$O (2.5M) | 2 ml |
| Glycine (20%) | 25 ml |
| Adjust volume to 1 L. | |

Following incubation for about two days in YEME medium, the cells were harvested and protoplasts were prepared as described by Hopwood, et al., 1985, *Genetic Manipulation of Streptomyces: A Laboratory Manual*, pp. 12–14. Lysozyme was dissolved in P buffer before use. The protoplasts, in P buffer, were stored frozen at −70° C. for a few days before fusion.

To conduct the fusion, the protoplasts were rapidly thawed from −70° C. stocks under running tap water. Approximately equal numbers of protoplasts of PGS 131 and PGS 132 were pipetted gently into a polycarbonate centrifuge tube. The volume in the tube was adjusted to 5.0 ml with P buffer.

| P buffer | |
|---|---|
| Base solution: | |
| Sucrose | 205 g |
| K$_2$SO$_4$ | 0.25 g |
| MgCl$_2$.6H$_2$O | 2.02 g |
| Distilled water to | 977 g |

Autoclave for 25 minutes at 121° C.

After autoclaving, add in order from sterile stocks of:

| | |
|---|---|
| KH$_2$PO$_4$ (0.5%) | 1 ml |
| Trace Element Solution* | 2 ml |
| CaCl$_2$.2H$_2$O (3.68%) | 10 ml |
| MES Buffer (1.0 M) | 10 ml |
| Adjust pH to 6.5; bring volume to 1 L. | |

*Trace Element solution is as described above in Part A.

Then, the protoplast fusion mixture was centrifuged at about 2000 g for 7 minutes. The supernatant was decanted carefully and the protoplast pellet was resuspended to a final volume of 200 µl with P buffer. To that suspension was added 800 µl of 50% PEG. The 50% PEG was prepared by autoclaving 1 g aliquots of PEG 1000 (Sigma Chemical Co., St. Louis, Mo. 63178) in glass vials, adding 1.0 ml of P buffer to each vial and heating the vial to 55° C. or, alternatively, the PEG was weighed, dissolved in P buffer and filter sterilized just prior to use. The fusion mixture was mixed by drawing it up into a Pasteur pipet and expelling it. The fusion was incubated for 2 minutes at room temperature. Then, 9 ml of P buffer was added to dilute the PEG. The fusion mixture was then centrifuged at about 2000 g for 7 minutes, the supernatant was decanted carefully and the fused, washed protoplasts were resuspended in 1.0 ml of P buffer. Serial dilutions of the fused protoplasts were prepared in P buffer. Then, 1.0 ml aliquots of the serial dilutions were spread gently over the surface of Mac Neil's RM14 regeneration medium (slightly modified) agar plates using disposable plastic loops.

| Mac Neil's RM14 regeneration medium (slightly modified) | |
|---|---|
| Base solution: | |
| Sucrose | 205 g |
| K$_2$SO$_4$ | 0.25 g |
| MgCl$_2$ · 6H$_2$O | 10.12 g |
| Glucose | 10 g |
| Difco Casaminoacids | 0.1 g |
| Difco Yeast Extract | 5.0 g |
| Difco Oatmeal Agar | 3.0 g |
| Difco Bacto Agar | 22.0 g |
| Distilled water to | 955 ml |
| Autoclave for 25 minutes at 121° C. | |
| After autoclaving, add sterile stocks of: | |
| KH$_2$PO$_4$ (0.5%) | 10 ml |
| CaCl$_2$ · 2H$_2$O | 5 ml |
| L-proline (20%) | 15 ml |
| MES buffer (1.0 M) | 10 ml |
| Trace Element Solution* | 2.0 ml |
| NaOH (1 N) | 3.0 ml |
| Adjust pH to 6.5; bring volume to 1 L. | |

*Trace Element Solution (per Liter):
| | |
|---|---|
| ZnCl$_2$ | 40 mg |
| FeCl$_3$ · 6H$_2$O | 200 mg |
| CuCl$_2$ · 2H$_2$O | 10 mg |
| MnCl$_2$ · 4H$_2$O | 10 mg |
| Na$_2$B$_4$O$_7$ · 10H$_2$O | 10 mg |
| (NH$_4$)$_6$Mo$_7$O$_{24}$ · 4H$_2$O | 10 mg |

Following incubation of the regeneration plates at about 30° C. for 8 days, it was found that the $10^0$, $10^{-1}$ and $10^{-2}$ dilution plates had essentially confluent lawns of growth. The $10^0$, $10^{-1}$, and $10^{-2}$ dilution plates were then used to respectively inoculate about 100 ml of AS-7 medium in separate 300 ml Erlenmeyer flasks. The flasks were incubated at about 30° C., 200 rpm for 2 days. The resulting AS-7 cultures were mixed 1:1 with 80% glycerol, titered on YPD agar and stored at −20° C. Due to contamination, the $10^0$ AS-7 culture was discarded. The culture titer from the $10^{-1}$ and $10^{-2}$ cultures yielded the same result of 1.5×$10^7$ colonies/ml. The colonies predominantly appeared typical, i.e., pigmented and soft, on YPD agar although about 1% of the colonies were small.

To select for recombinant (fused) colonies, the cultures were plated onto M9/glycerol plus syncasa plus pantothenate agar plates and incubated at about 30° C. for 5–7 days.

M9/glycerol Plus Syncasa Plus Pantothenate Agar

Glycerol 5 g
Agar 20 g
H$_2$O 900 ml
Autoclave 25 min. @ 121° C.
Add 100 ml of 10X M9 Salts Concentrate (minus divalent metal salts);
10 ml of syncasa (100 fold concentrate);
1 ml of D,L-pantothenate (1%), filter sterilized;
1 ml of sterile 1 M MgSO$_4$; and
1 ml of sterile 0.1 M CaCl$_2$.

10X M9 Salts Concentrate (Minus Divalent Metal Salts)

Na$_2$HPO$_4$ 60 g
KH$_2$PO$_4$ 30 g
NaCl 5 g
NH$_4$Cl 10 g
H$_2$O to 1 L
Autoclave 25 min. @ 121° C.

| Composition of "Syncasa" 100 fold Concentrate | |
|---|---|
| | grams/liter |
| L-alanine | 3 |
| L-arginine | 4 |
| L-aspartic acid | 6 |
| L-cystine | 1 |
| L-glutamic acid | 20 |
| glycine | 1 |
| L-histidine | 2 |
| L-isoleucine | 5 |
| L-leucine | 9 |
| L-lysine | 7 |
| L-methionine | 3 |
| L-phenylalanine | 6 |
| L-proline | 10 |
| L-serine | 6 |
| L-threonine | 4 |
| L-tyrosine | 4 |
| L-tryptophan | 1 |
| L-valine | 6 |

The mixture is adjusted to pH 7 and filter sterilized. One volume of concentrate is added to 99 volumes of medium to achieve standard use concentrations.

The recombinant colonies were easily recognized as large, healthy colonies of about 0.5 cm in diameter growing among a background of small, pinhead-sized colonies. The recombinants do not require arginine, uracil and guanosine for growth car$^+$, gua$^+$). It was observed that about 25% of the colonies of the $10^{-1}$ culture were car$^+$ and gua$^+$ (163 out of 575) when spread on M9/glycerol plus syncasa plus pantothenate agar from $-20°$ C., glycerol stored cells whereas about 13% of the $10^{-2}$ culture (10 out of 75) were car$^+$ and gua$^+$. Subsequent platings yielded lower titers of car$^+$, gua$^+$ recombinants which indicated some instability is associated with storing the recombinants in glycerol at $-20°$ C.

Numerous car$^+$, gua$^+$ recombinants were tested for the presence of branched-chain 2-oxo acid dehydrogenase activity according to the $^{14}CO_2$ procedure described above. Those recombinants which had such activity were tested for their requirement for isoleucine, leucine and valine (ilvE) on appropriate media as described above. Those recombinants which have branched-chain 2-oxo acid dehydrogenase activity and which require isoleucine, leucine and valine (ilvE) were screened for the absence of O-methyl transferase by culturing the recombinants in AP-5 medium with an appropriate precursor, such as 2-methylbutyrate or cyclohexanecarboxylic acid, and determining which cultures do not produce avermectin A type compounds. The HPLC procedure described above was used to assay for the presence of the avermectin compounds produced by the recombinants.

One such recombinant (209R38) was chosen as producing the best avermectin B levels in the absence of detectable avermectin A compounds. It was further found that 209R38 cannot utilize a mixture of isoleucine, leucine and valine (0.25–0.33% of each) as sole carbon sources, which is expected for ilvE mutants. That recombinant was studied to ascertain whether it contained the early ilv mutation of one of its parents. To accomplish this, recombinant 209R38 was "back-crossed" with a histidine requiring (his) mutant of ATCC 31272 which had been isolated during the mutagenesis aid selection procedures described above to produce mutant I-3. The "back-cross" was performed by protoplast fusion of mutant 209R38 and the his$^-$ mutant according to the fusion procedure described above. Recombinant colonies were selected on M9 salts/glycerol agar containing 0.1% each of the three branched-chain 2-oxo acids, 2-oxoisocaproic acid, 2-oxo-3-methylvaleric acid and 2-oxo-3-methyl butyric acid, but no histidine. On such medium his$^+$, ilvE$^+$ recombinants will grow whether or not they have an early ilv mutation, because the 2-oxo acids in the medium satisfy the auxotrophic requirement of such a mutation for isoleucine and valine. Upon replica plating of these recombinants to M9 salts/glycerol agar without the 2-oxo acids, some recombinants did not grow, indicating the presence of the early ilv mutation in strain 209R38.

Recombinant 209R38 (F.D. 28857, ATCC 55220) contains the early ilv mutation (branched-chain 2-oxo acid biosynthesis negative) and the ilvE (branched-chain amino acid transaminase negative) mutation and also lacks O-methyl transferase activity.

EXAMPLE 2

Alternative Method for Constructing *S. avermitilis* Lacking Branched-chain Amino Acid Transaminase Activity (ilvE) and Branched-chain 2-oxo Acid Biosynthetic Activity ("Early ilv") by Fusion An alternative route to construct *S. avermitilis* ilvE, early ilv double mutants comprises fusion of an avermectin producing ilvE strain with an avermectin producing, early ilv strain, one or both of which optionally can contain an additional and separate non-ilv auxotrophy such as a requirement for purine or lysine. The fusants are then conveniently selected by virtue of their prototrophy for the additional requirements and screened for the desired ilvE, early ilv double mutational genotype as described in Example 1.

EXAMPLE 3

Alternative Method for Constructing *S. avermitilis* Lacking Branched-chain Amino Acid Transaminase Activity (ilvE) and Branched-chain 2-oxo Acid Biosynthetic Activity ("Early ilv") By Mutation An avermectin producing strain of *S. avermitilis* is mutagenized according to standard methods well known to those skilled in the art and the mutants are screened for an early ilv mutation as described in Example 1. Once identified, the early ilv strain is then subjected to mutagenesis and the mutants are screened for an ilvE mutation also as described in Example 1.

EXAMPLE 4

Production of Avermectin B Compounds with *S. avermitilis* 209R38 (ATCC 55220)

To determine the ability of *S. avermitilis* ATCC 209R38 to produce avermectin B compounds by utilizing either branched-chain fatty acids or branched-chain 2-oxo acids as precursors, the following series of fermentations were conducted.

*S. avermitilis* 209R38 was used to inoculate 30 ml of AS-7 medium in a 300 ml Erlenmeyer flask which was then incubated with shaking at about 30° C. and 200 rpm for about 40 hours. Then, 2.5 ml of the culture were used to inoculate flasks containing 30 ml of AP-5 medium with the precursor shown in Table I, below, at 400 ppm in 300 ml Erlenmeyer flasks. The flasks were incubated with shaking at about 30° C. and 200 rpm for 20 days. The cultures were then extracted with solvent and analyzed for B avermectin production according to the HPLC procedure described above.

TABLE I

| PRECURSOR IN AP-5 MEDIUM | EXPECTED CORRESPONDING C-25 SUBSTITUENT | PRESENCE OF CORRESPONDING B AVERMECTIN* | |
| --- | --- | --- | --- |
| | | B1 | B2 |
| S(+)-2-methylbutyrate | sec-butyl | + | + |
| Isobutyrate | isopropyl | + | + |
| 2-oxo-3-methylvaleric acid | sec-butyl | + | + |
| 2-oxo-isovaleric acid | isopropyl | + | + |
| cyclohexylcarboxylic acid | cyclohexyl | + | + |
| cyclohexylglyoxalic acid | cyclohexyl | + | + |

*The B avermectins with the expected C-25 substituent in each case were the most prevalent compound present.

What is claimed is:

1. *Streptomyces avermitilis* lacking branched-chain amino acid transaminase activity, branched-chain 2-oxo acid biosynthetic activity and, optionally, avermectin B-O-methyl transferase activity.

2. *Streptomyces avermitilis* according to claim 1 lacking branched-chain amino acid transaminase activity, branched-chain 2-oxo acid biosynthetic activity and avermectin B-O-methyl transferase activity.

3. *Streptomyces avermitilis* according to claim 2 having the identifying characteristics of ATCC 55220.

4. *Streptomyces avermitilis* ATCC 55220.

5. A process for preparation of an avermectin which comprises aerobically fermenting a strain of *Streptomyces avermitilis* which lacks branched-chain amino acid transaminase activity and branched-chain 2-oxo acid biosynthetic activity in an aqueous nutrient medium comprising an assimilable source of nitrogen, carbon and inorganic salts and a compound capable of utilization in the biosynthesis of an avermectin.

6. A process according to claim 5 for the preparation of B-avermectins wherein the *S. avermitilis* has the identifying characteristics of ATCC 55220.

7. A process according to claim 5 wherein the compound is of the formula

wherein R is an alpha-branched-chain group, the carbon atom thereof to which is attached the —COOH group is also attached to at least two other atoms or groups other than hydrogen; or a precursor convertible to said compound during the fermentation process.

8. A process according to claim 7 wherein R is R' and R' is an alpha-branched $C_3$–$C_8$ alkyl, alkenyl, alkynyl, alkoxyalkyl or alkylthioalkyl group; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulfur containing heterocyclic ring which may be saturated, or fully or partially unsaturated and which may optionally be substituted by one or more $C_1$–$C_4$ alkyl groups or halo atoms, or a precursor convertible to said compound during the fermentation process.

9. A process according to claim 5 wherein the compound is of the formula

wherein R is —$CH_2R''$ and R'' is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy alkenyl or alkynyl groups may be substituted by one or more halo atoms; or a $C_3$–$C_8$ cycloalkyl or $C_5$–$C_8$ cycloalkenyl group, either of which may be substituted by methylene or one or more $C_1$–$C_4$ alkyl groups or halo atoms; or a 3 to 6 membered oxygen or sulphur containing heterocyclic ring which may be saturated, or fully or partially unsaturated and which may be substituted by one or more $C_1$–$C_4$ alkyl groups or halo atoms; or a group of the formula $SR^7$ wherein $R^7$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur containing heterocyclic ring which may be saturated, or fully or partially unsaturated and which may be substituted by one or more $C_1$–$C_4$ alkyl groups or halo atoms, or a precursor convertible to said compound during the fermentation process.

10. A process according to claim 8 wherein the compound convertible to RCOOH wherein R is R' is

wherein R' is as previously defined; n is 0, 2, 4 or 6; and Z is —$CH_2OH$, —CHO, —$COOR^5$, —$CH_2NH_2$ or —$CONHR^6$ wherein $R^5$ is H or ($C_1$–$C_6$)alkyl; and $R^6$ is hydrogen, ($C_1$–$C_4$)alkyl, —CH(COOH)$CH_2$COOH, —CH(COOH)($CH_2$)$_2$COOH or —CH(COOH)($CH_2$)$_2SCH_3$.

11. A process according to claim 8 wherein R' is
cyclobutyl;
cyclopentyl;
cyclohexyl;
cycloheptyl;
2-methylcyclopropyl;
3-cyclohexenyl;
1-cyclopentenyl;
1-cyclohexenyl;
3-methylcyclohexyl (cis/trans);
4-methylenecyclohexyl;
3-methylcyclobutyl;
3-methylenecyclobutyl;
3-cyclopentenyl;
1-cyclopropylethyl;
3-fluorocyclobutyl;
4,4-difluorocyclohexyl;
isopropyl;
sec-butyl;
2-pentyl;
2,3-dimethylpropyl;
2-hexyl;
2-pent-4-enyl;
2-methylthioethyl;
S-2-methylpentyl;
R-2-methylpentyl;
2-thienyl;
3-thienyl;
4-tetrahydropyranyl;
3-furyl;
2-chlorothienyl;
3-tetrahydrothienyl;
4-methylthio-2-butyl;
4-tetrahydrothiopyranyl;
4-methoxy-2-buty; or
4-methylthio-2-butyl.

12. A process according to claim 11 wherein R' is cyclohexyl.

13. A process according to claim 11 wherein R' is derived from a precursor convertible to R'—COOH during the fermentation, said compound being of the formula

wherein R' is as previously defined; n is 0, 2, 4 or 6; Z is —CH$_2$OH, —CHO, —COOR$^5$, —CH$_2$NH$_2$ or —CONHR$^6$ wherein R$^5$ is (C$_1$–C$_6$)alkyl; R$^6$ is hydrogen, (C$_{1-4}$)alkyl, —CH(COOH)CH$_2$COOH, —CH(COOH)(CH$_2$)$_2$COOH or —CH(COOH)(CH$_2$)$_2$SCH$_3$.

14. A process according to claim 9 wherein the precursor convertible to R—COOH wherein R is —CH$_2$R" is

wherein

Z' is CH$_2$OH, —CH$_2$NH$_2$, —COOH or —CHO;

n is 1, 3 or 5 when Z' is —CH$_2$OH, —CH$_2$NH$_2$ or —CHO; and n is 3 or 5 when Z' is —COOH.

15. A process according to claim 9 wherein R—COOH is methylthioacetic acid;
ethylthioacetic acid;
3-methylbutyric acid;
3-trifluoromethylbutyric acid;
3-methylpentanoic acid;
n-butyric acid;
cyclopentane acetic acid;
thiophene-3-acetic acid; or
propionic acid.

16. A process according to claim 8 for the preparation of B avermectins wherein the strain of *S. avermitilis* is *S. avermitilis* having the identifying characteristics of ATCC 55220.

17. A process according to claim 9 for the preparation of B avermectins wherein the strain of *S. avermitilis* is *S. avermitilis* having the identifying characteristics of ATCC 55220.

18. A process according to claim 5 wherein the compound is of the formula

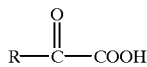

wherein R is an alpha-branched-chain group, the carbon atom thereof to which is attached the —COCOOH group is also attached to at least two other atoms or groups other than hydrogen; or a precursor convertible to said compound during the fermentation process.

19. A process according to claim 18 wherein R is R' and R' is an alpha-branched C$_3$–C$_8$ alkyl, alkenyl, alkynyl, alkoxyalkyl or alkylthioalkyl group; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methylene or one or more C$_1$–C$_4$ alkyl groups or halo atoms; or a 3 to 6 membered oxygen or sulfur containing heterocyclic ring which may be saturated, or fully or partially unsaturated and which may optionally be substituted by one or more C$_1$–C$_4$ alkyl groups or halo atoms, or a precursor convertible to said compound during the fermentation process.

20. A process according to claim 5 wherein the compound is of the formula

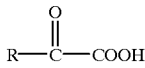

wherein R is —CH$_2$R" and R" is H, C$_1$–C$_8$ alkyl, C$_2$–C$_8$ alkenyl, C$_2$–C$_8$ alkynyl, alkoxyalkyl or alkylthioalkyl containing from 1 to 6 carbon atoms in each alkyl or alkoxy group, wherein any of said alkyl, alkoxy alkenyl or alkynyl groups may be substituted by one or more halo atoms; or a C$_3$–C$_8$ cycloalkyl or C$_5$–C$_8$ cycloalkenyl group, either of which may be substituted by methylene or one or more C$_1$–C$_4$ alkyl groups or halo atoms; or a 3 to 6 membered oxygen or sulphur containing heterocyclic ring which may be saturated, or fully or partially unsaturated and which may be substituted by one or more C$_1$–C$_4$ alkyl groups or halo atoms; or a group of the formula SR$^7$ wherein R$^7$ is C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, phenyl or substituted phenyl wherein the substituent is C$_1$–C$_4$ alkyl, C$_1$–C$_4$ alkoxy or halo, or a 3 to 6 membered oxygen or sulphur containing heterocyclic ring which may be saturated, or fully or partially unsaturated and which may be substituted by one or more C$_1$–C$_4$ alkyl groups or halo atoms, or a precursor convertible to said compound during the fermentation process.

21. A process according to claim 18 wherein the precursor convertible to RCOCOOH is

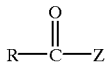

wherein R is R'; R' is an alpha-branched C$_3$–C$_8$ alkyl, alkenyl, alkynyl, alkoxyalkyl or alkylthioalkyl group; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methylene or one or more C$_1$–C$_4$ alkyl groups or halo atoms; or a 3 to 6 membered oxygen or sulfur containing heterocyclic ring which may be saturated, or fully or partially unsaturated and which may optionally be substituted by one or more C$_1$–C$_4$ alkyl groups or halo atoms; and Z is —CH$_2$OH, —CHO, —COOR$^5$, —CH$_2$NH$_2$ or —CONHR$^6$ wherein R$^5$ is H or (C$_1$–C$_6$)alkyl; and R$^6$ is hydrogen, (C$_1$–C$_4$)alkyl, —CH(COOH)CH$_2$COOH, —CH(COOH)(CH$_2$)$_2$COOH or —CH(COOH)(CH$_2$)$_2$SCH$_3$.

22. A process according to claim 20 wherein the precursor convertible to RCOCOOH is

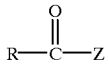

wherein R is —CH$_2$R"; R" is H, C$_1$–C$_8$ alkyl, C$_2$–C$_8$ alkenyl, C$_2$–C$_8$ alkynyl, alkoxyalkyl or alkylthioalkyl containing from 1 to 6 carbon atoms in each alkyl or alkoxy group, wherein any of said alkyl, alkoxy alkenyl or alkynyl groups may be substituted by one or more halo atoms; or a C$_3$–C$_8$ cycloalkyl or C$_5$–C$_8$ cycloalkenyl group, either of which may be substituted by methylene or one or more C$_1$–C$_4$ alkyl groups or halo atoms; or a 3 to 6 membered oxygen or sulphur containing heterocyclic ring which may be saturated, or fully or partially unsaturated and which may be substituted by one or more C$_1$–C$_4$ alkyl groups or halo atoms; or a group of the formula SR$^7$ wherein R$^7$ is C$_1$–C$_8$ alkyl, C$_2$–C$_8$ alkenyl, C$_2$–C$_8$ alkynyl, C$_3$–C$_8$ cycloalkyl, C$_5$–C$_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur containing heterocyclic ring which may be saturated, or fully or partially unsaturated and which may be substituted by one or more $C_1$–$C_4$ alkyl groups or halo atoms; and Z is —$CH_2OH$, —CHO, —$COOR^5$, —$CH_2NH_2$ or —$CONHR^6$ wherein $R^5$ is H or ($C_1$–$C_6$)alkyl; and $R^6$ is hydrogen, ($C_1$–$C_4$)alkyl, —CH(COOH)$CH_2$COOH, —CH(COOH)($CH_2$)$_2$COOH or —CH(COOH)($CH_2$)$_2$$SCH_3$.

23. A process according to claim 19 wherein

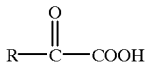

is cyclohexylglyoxalic acid.

24. A process according to claim 19 for the preparation of B avermectins wherein the strain of *S. avermitilis* is *S. avermitilis* having the identifying characteristics of ATCC 55220.

25. A process according to claim 20 for the preparation of B avermectins wherein the strain of *S. avermitilis* is *S. avermitilis* having the identifying characteristics of ATCC 55220.

* * * * *

UNITED STATES PATENT AND TRADEMARK OFFICE
CERTIFICATE OF CORRECTION

PATENT NO : 6,103,504
DATED : August 15, 2000
INVENTOR(S) : EDMUND W. HAFNER

It is certified that error appears in the above-identified patent and that said Letters Patent are hereby corrected as shown below:

Column 27, line 33, after "transaminase activity" delete "and"; and insert --,--;

Column 27, line 34, after "activity" insert --and, optionally, avermectin B-O-methyl transferase activity--;

Column 27, line 51, after "alkenyl," delete "alkynyl,";

Column 27, line 52, after "alkylthioalkyl group;" insert --an alpha-branched $C_4$-$C_8$ alkynyl group;--;

Column 29, line 5, after "$R^5$ is" insert --H or--;

Column 29, line 53, after "alkenyl," delete "alkynyl,";

Column 29, line 54, after "alkylthioalkyl group;" insert --an alpha-branched $C_4$-$C_8$ alkynyl group;--;

Column 30, line 34, after "alkenyl," delete "alkynyl,";

Column 30, line 34, after "alkylthioalkyl group;" insert --an alpha-branched $C_4$-$C_8$ alkynyl group;--.

Signed and Sealed this

First Day of May, 2001

Attest:

NICHOLAS P. GODICI

*Attesting Officer*   *Acting Director of the United States Patent and Trademark Office*